United States Patent
Zinkel

(10) Patent No.: US 7,163,532 B2
(45) Date of Patent: *Jan. 16, 2007

(54) SURGICAL INSTRUMENT WITH NEAR-AXIAL GEOMETRY

(75) Inventor: John L. Zinkel, St. Clair Shores, MI (US)

(73) Assignee: C&J Holdings, LLC, St. Clair Shores, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/266,982

(22) Filed: Nov. 4, 2005

(65) Prior Publication Data

US 2006/0064076 A1    Mar. 23, 2006

Related U.S. Application Data

(63) Continuation of application No. 10/331,205, filed on Dec. 30, 2002, now Pat. No. 6,962,582.

(51) Int. Cl.
*A61B 17/00* (2006.01)

(52) U.S. Cl. .......................................... 606/1; 433/124

(58) Field of Classification Search ............... 606/1, 606/41–52, 167, 169, 170, 201, 210; 433/124, 433/133, 157, 159
See application file for complete search history.

(56) References Cited

U.S. PATENT DOCUMENTS

| 3,994,301 | A | 11/1976 | Agris | 128/305 |
| 5,234,009 | A | 8/1993 | Lemon et al. | 132/329 |
| 5,531,749 | A | 7/1996 | Michelson | 606/93 |
| 5,589,183 | A | 12/1996 | Jannetta | 424/423 |
| 5,962,004 | A | 10/1999 | Jannetta | 424/423 |
| 6,096,026 | A | 8/2000 | Schultz | 606/1 |
| 6,131,228 | A | 10/2000 | Chen et al. | 15/22.1 |
| 6,458,143 | B1 | 10/2002 | Sugai | 606/169 |

FOREIGN PATENT DOCUMENTS

WO    WO 99/15084    4/1999

OTHER PUBLICATIONS

"Mizuho Skull Base Instrumentation", Brochure dated 1999.

*Primary Examiner*—Linda C. M. Dvorak
*Assistant Examiner*—Aaron Roane
(74) *Attorney, Agent, or Firm*—Gifford, Krass, Groh, Sprinkle, Anderson & Citkowski, P.C.

(57) ABSTRACT

A surgical instrument with near-axial geometry includes a linearly elongated handle portion having a handle axis defined along its length. The handle portion is joined to a linearly elongated working portion by an offset portion. The working portion includes a working axis defined along its length, and the working axis and handle axis intersect at an angle which is no greater than 5 degrees. In a specific embodiment, the base of the working tip of the working portion falls within 4 millimeters of the vertex of the angle.

7 Claims, 3 Drawing Sheets

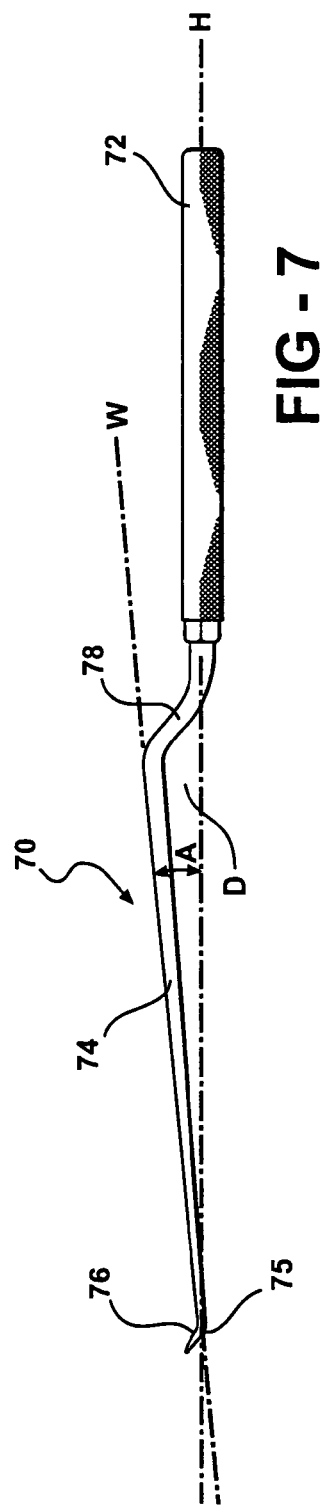
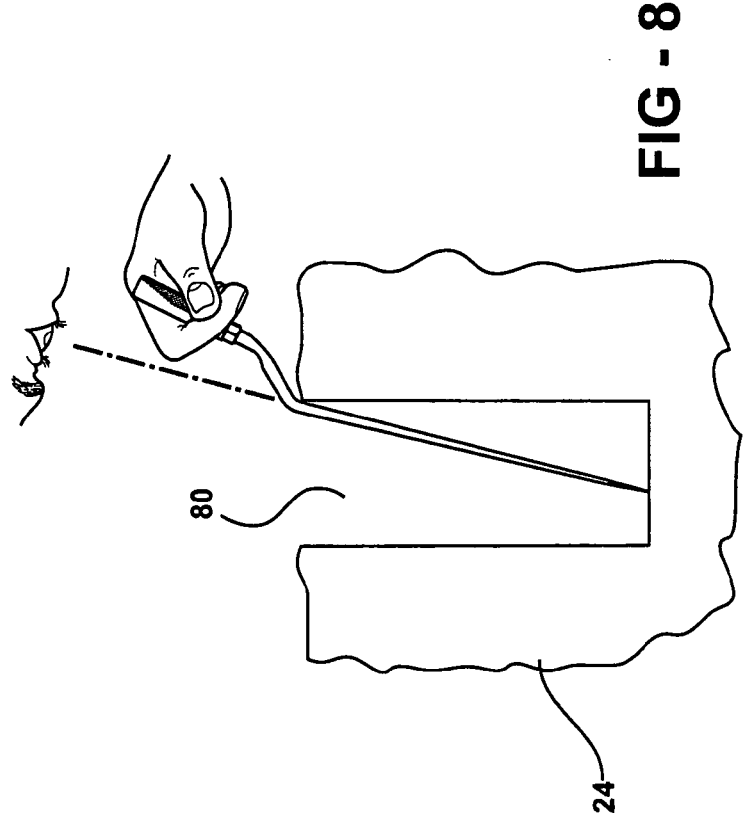

SURGICAL INSTRUMENT WITH NEAR-AXIAL GEOMETRY

RELATED APPLICATION

This application is a continuation of U.S. patent application Ser. No. 10/331,205 filed Dec. 30, 2002 and issued Nov. 8, 2005 as U.S. Pat. No. 6,962,582.

FIELD OF THE INVENTION

This invention relates generally to surgical instruments. More particularly, the invention relates to neurosurgical instruments. Most specifically, the invention relates to surgical instruments having a unique near-axial geometry, which instruments are advantageously employed in minimally invasive surgical procedures.

BACKGROUND OF THE INVENTION

Neurosurgical procedures generally involve very fine anatomical structures located in a densely featured environment. Consequently, neurosurgical procedures require a surgeon to carry out very fine micromanipulation techniques with a high degree of accuracy and precision so as to minimize any damage to adjoining neurological structures, which damage could have a very significant effect. Micromanipulation techniques, such as microdissection, curetting, suturing, and cutting with scissors or a scalpel, are involved, for example, in cranial surgery, surgery for acoustic neuromas, and spinal surgery, among others. In addition to the requirement for maintaining very fine control of the surgical procedure, it is increasingly desirable and advantageous to combine these microtechniques with ever smaller surgical exposures to minimize the invasiveness of such surgical procedures, and thereby to enhance patient recovery and surgical outcome.

Surgical instruments for microdissection and other micromanipulations are commonly used in brain and spine surgery, as well as in many other areas in human and veterinary medicine. These microinstruments, which include rongeurs, dissectors, scalpels, microscissors, needle drivers, suture holders, curettes, electrodes, probes, forceps, aneurysm clip applicators and the like, are being combined with new surgical exposure techniques that allow for surgery to be performed through ever smaller incisions, to improve patient outcome after surgery (since smaller incisions are easier to recover from). The prior art has developed a number of surgical instruments for carrying out microdissections and other fine procedures on neurological structures; however, as will be explained hereinbelow, the various approaches implemented by the prior art all entail various limitations, and are less than satisfactory.

Referring now to FIG. 1, there is shown a prior art neurosurgical instrument 10 of the type which has been widely used for many years for neurosurgical procedures. This is a straight shafted instrument in which the handle and working end share the same axis of rotation. Instruments of this type are available from a number of sources, for example the Rhoton dissectors sold by the Codman corporation. The instrument 10 is a generally linear instrument and it includes a handle portion 12 configured to be grasped and held by a surgeon. The handle portion 12 and the working portion 14 both lie along a common axis, hence the instrument 10 can be described as having axial geometry.

A working portion of the instrument 14 projects from the handle, and a working tip 16 is disposed at the end of the working portion 14 opposite the handle portion 12. As shown in FIG. 1, the working tip 16 is a slightly curved dissector blade. As is known in the art, there are a number of different configurations of working tips such as round knife blades, probes, blunt blades, curved blades, suture holders, needle holders, scissors, curettes and the like. It is to be understood that the various instrumentation described and discussed herein, including the instrumentation of the present invention, may be employed with variously configured working tips. The near axial geometry of the instruments of the present invention may be readily adapted to instruments having variously configured handles such as curved handles and the like provided that at least one of the profiles of the instrument exhibits the near axial geometry.

In the use of the straight shafted instrument 10, with the surgeon grasping the microinstrument handle 12, the working tip 16 of the instrument can be moved/manipulated in any direction in the surgical exposure including motion along the axis of the instrument, and in motions in a pendular direction, or in a circular direction, or quite importantly, in a rotary motion where the working tip 16 is gently rotated by the surgeon rotating the handle 12 of the instrument. As the handle 12 is rotated, the working tip 16 rotates along the same axis of rotation since handle 12 and working end 16 of the instrument share the same axis of rotation.

The problem with bringing a straight microdissector instrument into a small incision (with a high aspect ratio) is that as the instrument is used vertically within the surgical wound, the surgeon's hand is brought into the surgeon's line of sight down the instrument so that the hand blocks the surgeon's view of the working tip at the working end of the instrument. This problem becomes critically important since the thrust in modern surgery is to perform operations through ever narrower and ever less invasive surgical exposures.

Referring now to FIG. 2A, the instrument 10 of FIG. 1 is shown in use in a surgical channel 20 formed through a body of tissue 24. As will be seen, the surgical channel 20 must be relatively wide in order for the surgeon to view the surgical site. As noted above, wide channels are not preferred and this presents a significant problem with axial instruments of the type depicted in FIG. 1. As is shown in FIG. 2B, when the straight instrument 10 of FIG. 1 is used in a narrower channel 22, the instrument 10 and the surgeon's hand block the surgeon's view of the working tip 16 of the instrument. Procedures accomplished with straight instruments require a wider incision to allow for tipping of the instrument handle to move the surgeon's hand out of the line of sight to the instrument tip; and therefore, as a consequence of prior art instrument design, the surgery is more invasive to the patient than it need be.

In an effort to overcome the problems associated with straight instruments of the type shown in FIG. 1, the prior art has developed offset, bayonet type instruments. Bayonet instruments help solve problems of the prior art straight instruments to some extent. The bayonet handle offsets the hand away from the surgeon's line of sight along the working end of the instrument, thus the surgeon's line of sight is not blocked by his hand. This bayonet instrument design allows the surgeon to maintain an unobstructed view of the working tip, and also allows for all motions of the straight microdissector to be preserved except for the very important action of rotating the working tip by rotation of the surgeon's handle. Bayonet type instruments are known in the art and are available from a number of sources, as for example, the Yasargil line manufactured by the Aesculap Instrument Company. One such instrument is shown at reference numeral 30 in FIG. 3. The instrument 30 of FIG. 3 comprises microscissors, and includes a handle portion 32. It is to be noted that the handle 32 of the FIG. 3 instrument 30 is of somewhat different design than the handle of the instrument 10 of FIG. 1. It is to be understood that the various prior art instruments illustrated herein, as well as the instruments of the present invention, may have handles variously configured, including handles configured as depicted herein as well as handles otherwise configured.

The instrument 30 of FIG. 3 includes a working portion 34 having a working tip 36 comprising microscissor blades at one end thereof. The working portion 34 and handle portion 32 are offset from one another by an offset portion 38. Commonly, as here, the prior art instrument of FIG. 3 is configured so that an axis extending along the length of the handle (the handle axis), as is designated by line HH, and an axis extending along the length of the working portion (the working axis), as is designated by line WW, are generally parallel.

FIG. 4 depicts the instrument 30 of FIG. 3 as being used in a surgical procedure carried out through a passage 40 formed through the tissue 24 of a patient. As will be seen, the offset (38) between the handle portion 32 and working portion 34 improves the surgeon's view of the working tip 36 of the instrument and allows for the use of a somewhat narrower surgical passageway 40 than does the instrument 10 of FIG. 1. Also, the bayonet instrument can allow the surgeon to advance or withdraw the working tip 36 from the surgical field; and also, the handle can be swung in a pendulum fashion exactly as for a straight shafted instrument. In the bayonet configuration, however, axial rotation of the working tip, as can be accomplished with axial instruments, is no longer possible.

This inability to rotate the working tip is very significant, and results from the fact that the handle axis HH and working axis WW of the device 30 of FIG. 3 are parallel and separated. When the bayonet handle 32 is rotated, the working shaft 34 and working tip 36 become rotated in crankshaft fashion about the circumference of a circle, the center of which is the axis of rotation H of the handle. Any attempt to rotate the working end 36 and tip of the instrument similarly to the straight handled instrument becomes extremely impractical. It is extremely difficult to rotate the handle in a crankshaft fashion maintaining the working end of the instrument as the center of the axis of rotation. Thus the bayonet instrument design makes impossible controlled rotation of the working end of the instrument in turn to rotate the working tip, and compromises the precision of the surgical process.

An alternative way to offset the hand from the surgeon's line of sight down the working tip of the instrument, for example, is to bend the straight shaft instrument 10, of FIG. 1, sharply by 10 to 15 degrees mid-shaft at the junction between the working end and the surgeon's handle. This was done by Janetta in the design of his brain microdissector instruments, which instruments are commercially available from the Mueller Corporation. The problem, however, is that these types of instruments do not regain for the surgeon the ability to rotate the instrument handle and still rotate the working tip along a shared axis of rotation.

A hybrid bayonet instrument design combines the bayonet design as by Yasargil and the offset design as by Janetta. In this design, the working tip and the surgeon's handle do share the same axis of rotation. However, the shoulder of the instrument is so substantially offset from the surgeon's handle, that when the handle is rotated, the instrument shoulder could abut against structures in the wound. This in turn could cause the working tip to become displaced with the consequence of patient injury.

Referring now to FIG. 5, there is shown one such hybrid bayonet instrument 50 of the prior art. Instruments of this type are available under the designation "Fukushima Instruments" from Mizuho Medical Co., Ltd. As in the FIG. 4 instrument, the instrument 50 of FIG. 5 includes a handle portion 52 and a working portion 54, which terminates in a working tip 56. An offset portion 58 joins the handle 52 and working portion 54 so that the working axis WW and handle axis HH intersect at an angle A, which angle A is over 5 degrees. The offset is such that, in a typical instrument, the maximum spacing between the working portion 54 and handle axis HH is more than 10 millimeters. It is also notable that the vertex of the angle A formed by the handle axis HH and working axis WW is removed by a distance of at least several centimeters from the working tip 56.

Referring now to FIG. 6, the instrument 50 of FIG. 5 is shown in use. As shown in FIG. 6, the instrument 50 is disposed in a surgical channel 53 formed through the tissue 24 of a patient. In this instrument die offset portion 58 is relatively large, offsetting the surgeon's hand from his line of sight to the working tip. However, once the handle is rotated, the shoulder portion 59, of the offset rotates over a broad radius within the surgical channel/exposure thereby colliding with the wound edges, potentially deflecting the tip of the working end into critical structures.

Accordingly, despite various attempts in the prior art, there are no surgical instruments available that offset the surgeon's hand successfully away from his line of sight down the instrument to the working tip and yet which can preserve the surgeon's ability to rotate the handle and the working tip effectively as is achieved by a straight axis microdissector. As will be described in greater detail hereinbelow, the present invention provides surgical instruments which fulfill these requirements.

BRIEF DESCRIPTION OF THE INVENTION

There is disclosed herein a neurosurgical instrument having near-axial geometry. The instrument comprises an elongated handle portion having a handle axis defined along its length, and a linearly elongated working portion having a working axis defined along its length. The working portion terminates in a working end. The working portion is joined to the handle portion in an angled relationship by an offset portion so that the handle axis and the working axis intersect to form an angle "A" which is greater than 0 and no more than 5 degrees. In specific embodiments, the distal most end of the working portion, to which the working tip is joined, is disposed proximate the vertex of the angle A, and in specific embodiments, it is within less than 10 millimeters of the vertex. In certain embodiments, the end is within 4 millimeters of the vertex. In a particular embodiment, the working end of the working portion, as well as the base (origin) any working tip associated therewith, is at the vertex. In specific configurations, the offset portion is configured such that no part of the working portion of the device is more than 10 millimeters from the handle axis.

BRIEF DESCRIPTION OF THE DRAWINGS

FIG. 7 depicts one embodiment of surgical instrument of the present invention; and FIG. 8 depicts the instrument of FIG. 7 in use.

DETAILED DESCRIPTION OF THE INVENTION

Figure 5:
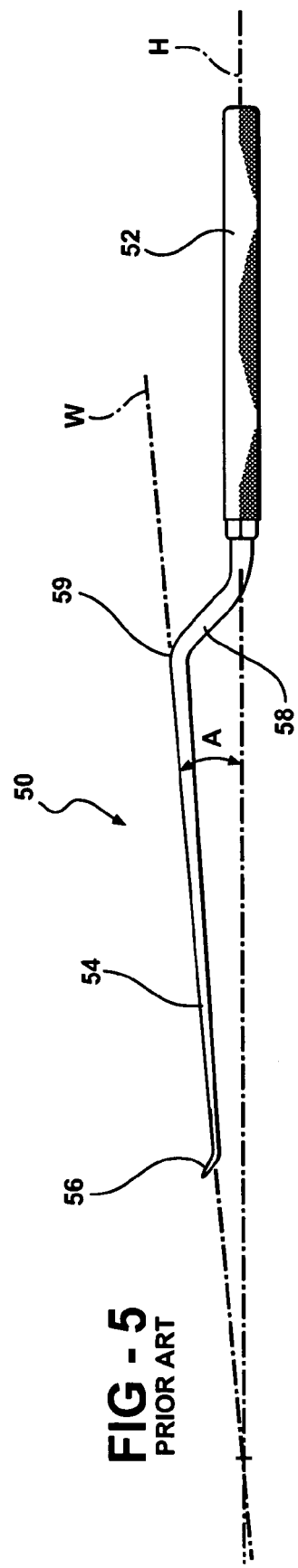
FIG. 5 depicts yet another prior art surgical instrument.

Referring now to FIG. 7, there is shown a near-axial neurosurgical instrument 70 structured in accord with the principles of the present invention. While the surgical instrument 70 of FIG. 7 bears some superficial resemblance to prior art instruments, particularly the instrument 50 of FIG. 5, there are a number of significant differences in structure between the two, and these differences are more than quantitative; since, as will be described in detail hereinbelow, they cause the instruments of the present invention to have qualitatively different performance characteristics as compared to prior art instrumentation.

The instrument 70 of the present invention includes a handle portion 72 and working portion 74 having a working end 75, with a tip 76 at the end thereof. As will be explained hereinbelow, the working tip 76 may be variously sized and configured. As in the previous embodiment, the handle portion 72 and working portion 74 are joined together in an angled relationship by an offset portion 78, having a shoulder portion 79, so that the handle axis HH and working axis WW intersect to form an angle A. It is significant that this angle A is no more than 5 degrees. As a consequence, the offset between the working axis WW and handle axis HH is relatively minor; hence, the instrumentation of the present invention is referred to as having "near-axial" geometry wherein the axis of the handle and the axis of the working portion are very close to coincident. As will be explained hereinbelow, this near-axial geometry provides for very good visibility while assuring precise control of the working tip of the instrumentation. The relative size of the handle portion and working portion of the instrument will depend upon the particular surgeon's preference, and particular procedure for which it is being employed; however, in most instances, the length of the instrument and the size of angle A will be such that no part of the working portion 74 will be spaced from the handle axis HH by a distance (D) which is greater than 1 centimeter. In particular embodiments, the distance D will be no greater than 7 millimeters.

Figure 1:
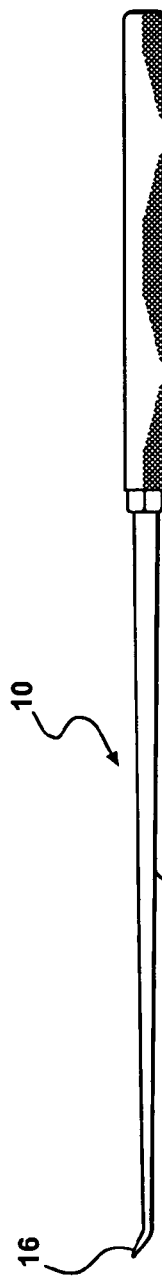
FIG. 1 depicts a prior art neurosurgical instrument.
Figure 2A:
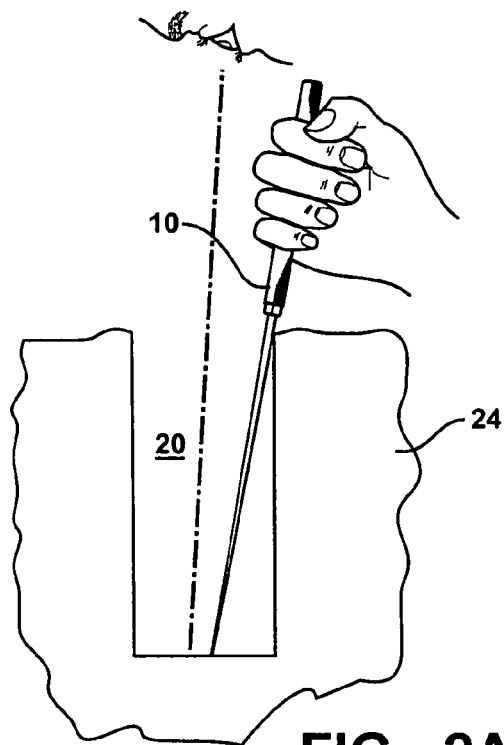
FIGS. 2A and 2B depict the prior art instrument of FIG. 1 in use.
Figure 2B:
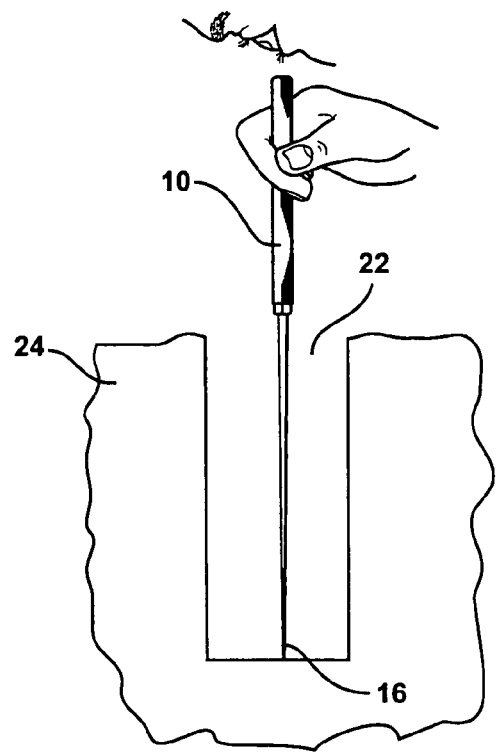

FIG. 8 depicts the instrument 70 being used in a surgical procedure carried out through a passageway 80 formed through the tissue 24 of a patient. As will be noted, the passageway 80 of FIG. 8 is relatively narrow as compared to the passageways 22, 40 and 52 required by prior art instrumentation. In fact, the passageway 80 is generally similar in size to the passageway 22 in FIG. 2B used with the straight instrument 10 of FIG. 1. Thus, the instrument is formed into a near vertical position, yet the handle is sufficiently offset so that the surgeon's hand does not block his view of the working tip; and yet, the handle 72 can be rotated without causing significant crankshafting of the working tip 76 of the working end and/or of the shoulder 79 of the instrument offset.

Figure 4:
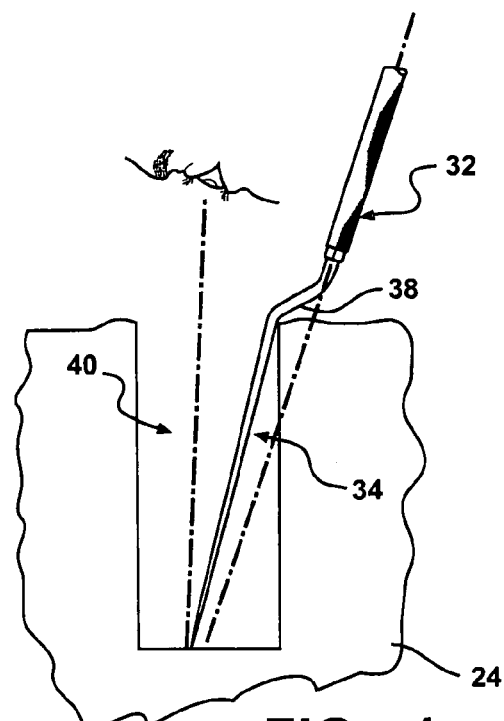
FIG. 4 depicts the prior art instrument of FIG. 3 in use.
Figure 6:
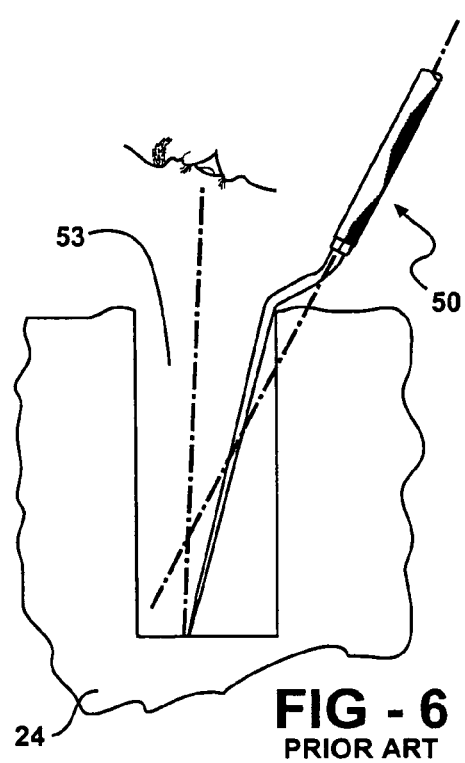
FIG. 6 depicts the prior art instrument of FIG. 5 in use.

In summary, the near-axial geometry of the instrument 70 of the present invention provides the surgeon with good visibility of the surgical field, and minimizes interference between the instrument and the walls of the surgical passageway 80. It is also very significant that the near-axial geometry allows for the instrument to be rotated about the handle axis without causing the working end, working tip, working portion and/or shoulder thereof to sweep out a large circular path as is shown in the FIG. 4 and FIG. 6 depictions. This combination of geometric features maximizes the surgeon's visibility as well as the precision and accuracy of the movement of the working tip of the surgical instrument.

Figure 3:
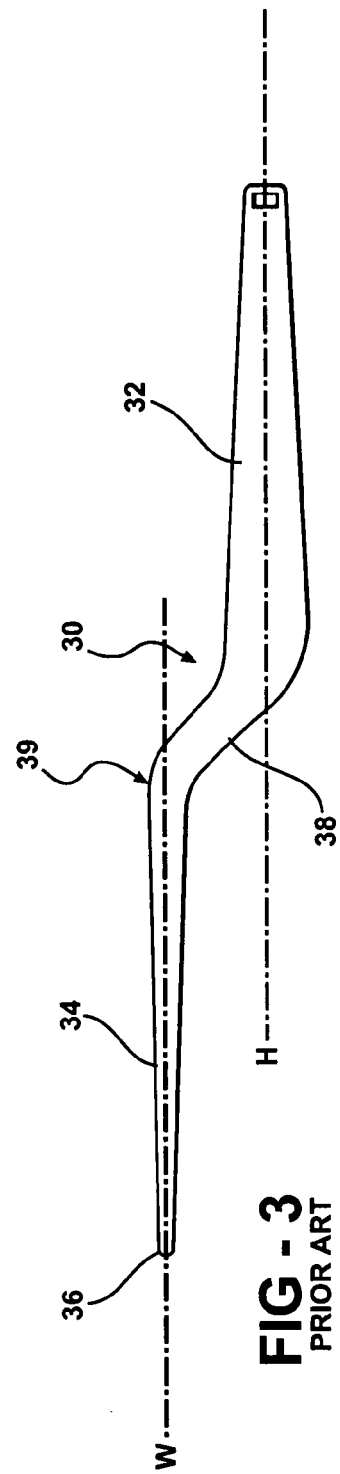
FIG. 3 depicts another embodiment of prior art surgical instrument.

As shown in the figure, the working end of the working portion 74 of the instrument 70 falls at the vertex of the angle A, and in most embodiments of the present invention, the working end will be within 10 millimeters, and in specific embodiments, within 4 millimeters of this vertex. A geometric arrangement of this type assures that the instrument will function like the straight, axial instrument 10 of FIG. 1 when rotated about the handle axis HH, and will not sweep out a circular pattern as occurs with instruments of the type shown in FIGS. 3 and 5.

It will thus be seen that the near-axial instrumentation of the present invention improves a surgeon's view of a surgical field while preserving precision and accuracy of motion and allowing surgery to be carried out through a relatively small opening. As such, the near-axial surgical instrumentation of the present invention marks a qualitative improvement over prior art instrumentation.

The instrumentation of the present invention may be implemented in embodiments other than those depicted herein. For example, as noted hereinabove, the handle portion of the instrumentation may be variously configured depending upon a surgeon's requirements and preferences. Also, the actual working tips of the instruments may be configured as rongeurs, dissectors, scalpels, microscissors, needle drivers, suture holders, curettes, electrodes, probes, forceps, aneurysm clip applicators and the like as is known and required in the art. As will be apparent to one of skill in the art, the handle portion of the instrument may be modified as is necessary to accommodate the form and function of the working tip. For example, if the tip is configured as scissors or forceps, the handle will need to be operable to actuate the working tip. Also, while the present invention has been described with reference to neurosurgical instruments, the principles of near axial geometry may be employed in any surgical instruments, including microsurgical instruments as well as instruments utilized in open surgery which is carried out without magnification. All of such embodiments, provided that they include the near-axial geometry of the present invention, in at least one profile, are included within the scope of this invention. The foregoing drawings, discussion and description are illustrative of specific embodiments, but are not meant to be limitations upon the practice thereof. It is the following claims, including all equivalents, which define the scope of the invention.

The invention claimed is:

1. A surgical instrument having near-axial geometry, said instrument comprising:

a linearly elongated handle portion having a central handle axis defined along the length thereof;

a linearly elongated working portion having a central working axis defined along the length thereof, said working portion terminating in a working end;

an offset portion which joins said working portion and said handle portion in an angled relationship so that said handle axis and said working axis form an angle "A" which is greater than 0 and no more than 5 degrees; and a working tip projecting from said working end at an angle with regard to the central handle axis and said central working axis, said working tip being selected from the group consisting of: rongeurs, dissectors, scalpels, microscissors, needle drivers, suture holders, curettes, electrodes, probes, forceps, and aneurysm clip holders.

2. The surgical instrument of claim 1, wherein said working end is disposed at the vertex of said angle A.

3. The surgical instrument of claim 1, wherein said working end is within 10 millimeters of the vertex of said angle A.

4. The surgical instrument of claim 1, wherein said working end is within 4 millimeters of the vertex of said angle A.

5. The surgical instrument of claim 1, wherein no point on said working portion is spaced from said handle axis by a distance of more than 10 millimeters.

6. The surgical instrument of claim 1, wherein no point on said working portion is spaced from said handle axis by a distance of more than 7 millimeters.

7. The surgical instrument of claim 1, wherein said working tip has a length dimension which is no greater than 6 millimeters.

* * * * *